(12) United States Patent
Roessl et al.

(10) Patent No.: US 11,096,639 B2
(45) Date of Patent: Aug. 24, 2021

(54) PROJECTION DATA ACQUISITION APPARATUS AND SUBJECT SUPPORT DEVICE

(71) Applicant: KONINKLIJKE PHILIPS N.V., Eindhoven (NL)

(72) Inventors: Ewald Roessl, Ellerau (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/466,308

(22) PCT Filed: Dec. 7, 2017

(86) PCT No.: PCT/EP2017/081868
§ 371 (c)(1),
(2) Date: Jun. 4, 2019

(87) PCT Pub. No.: WO2018/104469
PCT Pub. Date: Jun. 14, 2018

(65) Prior Publication Data
US 2020/0069267 A1 Mar. 5, 2020

(30) Foreign Application Priority Data
Dec. 9, 2016 (EP) .................................... 16203124

(51) Int. Cl.
*A61B 6/00* (2006.01)
*A61B 6/03* (2006.01)
(Continued)

(52) U.S. Cl.
CPC ............ *A61B 6/4291* (2013.01); *A61B 6/032* (2013.01); *A61B 6/0487* (2020.08);
(Continued)

(58) Field of Classification Search
CPC ..... A61B 6/032; A61B 6/0407; A61B 6/0457; A61B 6/4035; A61B 6/4291; A61B 6/484; A61B 6/5205; A61B 6/0487; G21K 1/067
See application file for complete search history.

(56) References Cited

U.S. PATENT DOCUMENTS

| 7,532,704 B2 | 5/2009 | Hempel |
| 7,535,986 B2 * | 5/2009 | Hempel ............ A61B 5/02007 378/4 |

(Continued)

FOREIGN PATENT DOCUMENTS

WO   WO2015132095 A1   9/2015

OTHER PUBLICATIONS

PCT International Search Report, International application No. PCT/EP2017/081868, dated May 16, 2018.

(Continued)

*Primary Examiner* — Dani Fox
*Assistant Examiner* — Soorena Kefayati
(74) *Attorney, Agent, or Firm* — Larry Liberchuk (57) ABSTRACT

The invention relates to a subject support device (1) to be used in a projection data acquisition apparatus (2) for acquiring projection data of a subject (3). The subject support device comprises a support component (4) providing a support surface (5) for supporting the subject while acquiring the projection data, a diffraction grating (6) for diffracting x-rays, and a moving unit (7, 8) for moving the support component and the diffraction grating relative to each other. This relative movement can allow for a movement of the support component such that the subject is moved through x-rays (16) for determining projection data of different parts of the subject, while the diffraction grating can still be traversed by the x-rays. These projection data can (Continued)

be used for generating a relatively large phase-contrast and/or dark-field projection image.

15 Claims, 2 Drawing Sheets

(51) Int. Cl.
    *G21K 1/06*     (2006.01)
    *A61B 6/04*     (2006.01)

(52) U.S. Cl.
    CPC .......... *A61B 6/4035* (2013.01); *A61B 6/5205* (2013.01); *G21K 1/067* (2013.01)

(56) References Cited

U.S. PATENT DOCUMENTS

| | | | |
|---|---|---|---|
| 8,009,796 B2 | 8/2011 | Popescu | |
| 9,084,528 B2 | 7/2015 | Geller | |
| 10,074,451 B2* | 9/2018 | Kottler | G02B 5/1838 |
| 2007/0183559 A1* | 8/2007 | Hempel | G21K 1/06 |
| | | | 378/4 |
| 2007/0183583 A1* | 8/2007 | Baumann | A61B 6/4233 |
| | | | 378/145 |
| 2007/0189456 A1* | 8/2007 | Haras | A61B 6/08 |
| | | | 378/98.5 |
| 2012/0188556 A1* | 7/2012 | Nagai | G21K 1/06 |
| | | | 356/521 |
| 2012/0236992 A1* | 9/2012 | Engel | A61B 6/484 |
| | | | 378/62 |
| 2012/0288056 A1* | 11/2012 | Murakoshi | A61B 6/5241 |
| | | | 378/37 |
| 2014/0169522 A1 | 6/2014 | Hoshino | |
| 2016/0113610 A1* | 4/2016 | Freudenberger | A61B 6/0492 |
| | | | 378/36 |
| 2016/0354046 A1* | 12/2016 | Freudenberger | A61B 6/4291 |
| 2017/0014091 A1* | 1/2017 | Mertelmeier | A61B 6/484 |
| 2017/0325765 A1* | 11/2017 | Kido | A61B 6/06 |
| 2017/0343486 A1* | 11/2017 | Tanabe | A61B 6/4476 |
| 2017/0372472 A1* | 12/2017 | Takahashi | G16H 50/30 |
| 2018/0035961 A1* | 2/2018 | Bartl | A61B 6/484 |

OTHER PUBLICATIONS

Kottler C. et al., "Grating Interferometer Based Scanning Setup for Hard X-Ray Phase Contrast Imaging", Review of Scientific Instruments, vol. 78, issue 4, pp. 43710, Apr. 2007.

Koehler T. et al., "Slit-Scanning Differential X-Ray Phase-Contrast Mammography: Proof-of-Concept Experimental Studies", American Association of Physicists in Medicine, Medical Physics, vol. 42, issue 4, pp. 1959-1965, Apr. 2015.

* cited by examiner

FIG. 1

FIG. 2

PROJECTION DATA ACQUISITION APPARATUS AND SUBJECT SUPPORT DEVICE

FIELD OF THE INVENTION

The invention relates to a subject support device for supporting a subject, a projection data acquisition apparatus for acquiring projection data of a subject and a computed tomography imaging system for generating a computed tomography image of a subject. The invention relates further to a projection data acquisition method and a computer program for acquiring projection data of a subject, and to a method for equipping a subject support device.

BACKGROUND OF THE INVENTION

Two-dimensional radiography systems can generally not generate phase-contrast or dark-field projection images of relatively large objects like the lung. Problematic are, for instance, the required atypical scanning geometry and difficulties in providing a large area gapless tiling of gratings to cover the relatively large field of view of, for example, 43 cm×43 cm.

US 2012/0288056 A1 discloses an x-ray imaging system with an x-ray source, first and second absorption gratings and a flat panel detector to obtain a phase contrast image of an object by performing imaging while moving the second absorption grating in a direction relative to the first absorption grating.

WO 2015/132095 A1 discloses an x-ray device and supplementary system for interferometric x-ray imaging of a patient with an x-ray device for generating projective absorption recordings with an emitter-detector system. The system comprising a focus-forming x-ray tube, a digital flat detector, a mobile grating attachment having a first interferometric x-ray grating and a second interferometric x-ray grating and a displacement device for displacing the second x-ray grating.

US 2007/0183559 A1 discloses an x-ray CT system for producing tomographic phase contrast and absorption images including a) a gantry having a stationary stator and a first rotor supported on the stator and rotating relative to the stator about a system axis and b) at least one set of x-ray optical gratings for determining phase contrast.

SUMMARY OF THE INVENTION

It is an object of the present invention to provide a subject support device for supporting a subject, a projection data acquisition apparatus for acquiring projection data of the subject and a computed tomography imaging system for generating a computed tomography image of the subject, which allow for an improved generation of phase-contrast and/or dark-field projection images. It is a further object of the present invention to provide a projection data acquisition method and a computer program for acquiring projection data of a subject, and a method for equipping a subject support device, which allow for an improved generation of phase-contrast and/or dark-field projection images.

In a first aspect of the present invention a subject support device for supporting a subject is presented, wherein the subject support device is adapted to be used in a projection data acquisition apparatus for acquiring projection data of the subject and wherein the subject support device comprises:

a support component providing a support surface for supporting the subject while acquiring the projection data, a diffraction grating for diffracting x-rays, and a moving unit for moving the support component and the diffraction grating relative to each other.

Since the support component and the diffraction grating are moved relative to each other by the moving unit, a movement of the support component, for instance, in order to move the subject through x-rays generated by an x-ray tube of the projection data acquisition apparatus, can be decoupled from a movement of the diffraction grating. In particular, the movement of the support component for moving the subject through the x-rays can be used for determining projection data of different parts of the subject, while, due to the decoupling, the diffraction grating can still be traversed by the x-rays. These projection data can be used for generating a relatively large phase-contrast and/or dark-field projection image.

Moreover, since the diffraction grating is a part of the subject support device, which is, for instance, a patient table, the diffraction grating does not need to be arranged on, for example, a rotor of a gantry of a projection data acquisition apparatus, thereby reducing the number of components to be integrated in the gantry. This can allow for a smaller gantry and less technical efforts for accurately rotating the components integrated in the gantry.

The subject is preferentially a human patient. However, the subject can also be an animal or a technical subject like baggage, wherein the projection data acquisition apparatus can be used for baggage inspection purposes.

The diffraction grating is preferentially a phase grating. However, it can also be an absorption grating. The diffraction grating is preferentially adapted to be used together with a further grating, which can be regarded as being an analyzer grating, for acquiring phase-contrast and/or dark-field projection data in a known way. The diffraction grating is preferentially integrated in the support component. The moving unit is preferentially adapted to move the support component and the diffraction grating in opposite directions. In particular, the support component comprises a longitudinal axis, wherein the moving unit is adapted to move at least one of the diffraction grating and the support component parallel to the longitudinal axis, i.e. the respective moving direction can be on the longitudinal axis or can have a distance to the longitudinal axis.

The subject support device can comprise a support foot to be positioned on a floor, wherein the moving unit can be adapted to move at least one of the support component and the diffraction grating relative to the support foot. Furthermore, the moving unit can be adapted to move at least one of the support component and the diffraction grating such that the diffraction grating remains stationary relative to the support foot. Thus, the subject can be moved through the x-rays such that sequentially different parts of the subject are traversed by x-rays generated by an x-ray tube, in order to generate projection data of different parts of the subject, wherein the x-rays still traverse the stationary diffraction grating. These projection data, which correspond to different parts of the subject, can then be combined for generating a phase-contrast and/or dark-field projection image, which can also be regarded as being a phase-contrast and/or dark-field scout image, respectively, and which shows the different parts of the subject. It is to be understood that the expression "at least one of A and B" and the expression "A and/or B" include a) A without B, b) B without A, and c) A and B.

The moving unit can also be adapted to move the diffraction grating in a direction being transverse to the longitudinal axis. In particular, the moving unit can be adapted to move the diffraction grating in a direction being orthogonal to the longitudinal axis. The moving unit and the diffraction grating are preferentially arranged such that the diffraction grating can be moved completely outside of x-rays generated by an x-ray tube of a projection data acquisition apparatus, in order to allow the projection data acquisition apparatus to acquire attenuation projection data and not only phase-contrast and/or dark-field projection data.

In a further aspect of the present invention a projection data acquisition apparatus for acquiring projection data of a subject is presented, wherein the projection data acquisition apparatus comprises:

a subject support device as defined in claim 1 for supporting the subject while acquiring the projection data, an x-ray tube for providing x-rays for traversing the subject and the diffraction grating of the subject support device, and an x-ray detector for detecting the x-rays after having traversed the subject and the diffraction grating and for generating the projection data.

The projection data acquisition apparatus can comprise a further grating, wherein the further grating is arranged such that the x-rays traverse the further grating, after the subject and the diffraction grating have been traversed by the x-rays, and the x-ray detector detects the x-rays after having traversed the subject, the diffraction grating and the further grating for generating the projection data. The further grating is preferentially a so-called "analyzer grating" to be used for generating phase-contrast and/or dark-field projection data. It is preferentially an absorption grating. The analyzer grating can be attached to the x-ray detector. By also using the analyzer grating for generating the phase-contrast and/or dark-field projection data the spatial resolution required by the x-ray detector can be decreased, thereby allowing for a technically simpler x-ray detector.

In an embodiment the subject support device comprises a support foot to be positioned on a floor, wherein the projection data acquisition apparatus comprises a controller for controlling the subject support device such that the moving unit of the subject support device moves the support component relative to the support foot and hence relative to the x-ray tube, in order to allow the x-rays to traverse different parts of the subject and the x-ray detector to generate projection data of the different parts of the subject, while the diffraction grating remains stationary relative to the support foot and hence relative to the x-ray tube, in order to allow the x-rays to traverse the diffraction grating while traversing the different parts of the subject. The projection data acquisition apparatus preferentially further comprises an image generation unit for generating a projection image showing the different parts of the subject based on the generated projection data. This allows for a generation of a phase-contrast and/or dark-field scout image showing different parts of the subject along a longitudinal axis of the subject, i.e. the different parts of the subject are transversely traversed by the x-rays and the resulting phase-contrast and/or dark-field projection data, respectively, are combined for generating a projection image of all traversed parts of the subject along the longitudinal axis.

In a further aspect of the present invention a computed tomography imaging system for generating a computed tomography image of a subject is presented, wherein the computed tomography imaging system comprises:

a projection data acquisition apparatus as defined in claim 8 for acquiring projection data of the subject, wherein the diffraction grating is movable such that the x-rays provided by the x-ray tube do not traverse the diffraction grating, wherein the projection data acquisition apparatus is adapted to rotate the x-ray tube around the support component, in order to allow the x-rays generated by the x-ray tube to traverse the subject in different acquisition directions and the x-ray detector to generate projection data corresponding to the different acquisition directions, and a reconstruction unit for reconstructing the computed tomography image based on the acquired projection data.

Since the diffraction grating is movable such that the x-rays provided by the x-ray tube do not traverse the diffraction grating, the computed tomography imaging system can be used for at least two purposes, a) generating phase-contrast projection images and/or dark-field projection images and b) acquiring attenuation projection data and reconstructing a computed tomography image based on the acquired attenuation projection data.

In a further aspect of the present invention a method of equipping a subject support device of an attenuation projection data acquisition apparatus is provided, wherein the subject support device includes a support component providing a support surface for supporting the subject while acquiring the projection data, wherein the method includes equipping the subject support device with a diffraction grating for diffracting x-rays and with a moving unit for moving the support component and the diffraction grating relative to each other.

In a further aspect of the present invention a projection data acquisition method for acquiring projection data of a subject by using the projection data acquisition apparatus as defined in claim 8 is presented, wherein the projection data acquisition method comprises:

supporting the subject by using the subject support device of the projection data acquisition apparatus and moving a) the support component of the subject support device and b) the diffraction grating of the subject support device relative to each other while acquiring the projection data, providing x-rays for traversing the subject and the diffraction grating in the subject support by the x-ray tube of the projection data acquisition apparatus, detecting the x-rays after having traversed the subject and the diffraction grating and generating the projection data based on the detected x-rays by the x-ray detector of the projection data acquisition apparatus.

In another aspect of the present invention a computer program for acquiring projection data of a subject is presented, wherein the computer program comprises program code means for causing a projection data acquisition apparatus as defined in claim 1 to carry out the steps of the projection data acquisition method as defined in claim 14, when the computer program is run on a computer controlling the projection data acquisition apparatus.

It shall be understood that the subject support device of claim 1, the projection data acquisition apparatus of claim 8, the computed tomography imaging system of claim 12, the method of equipping a subject support device of claim 13, the projection data acquisition method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
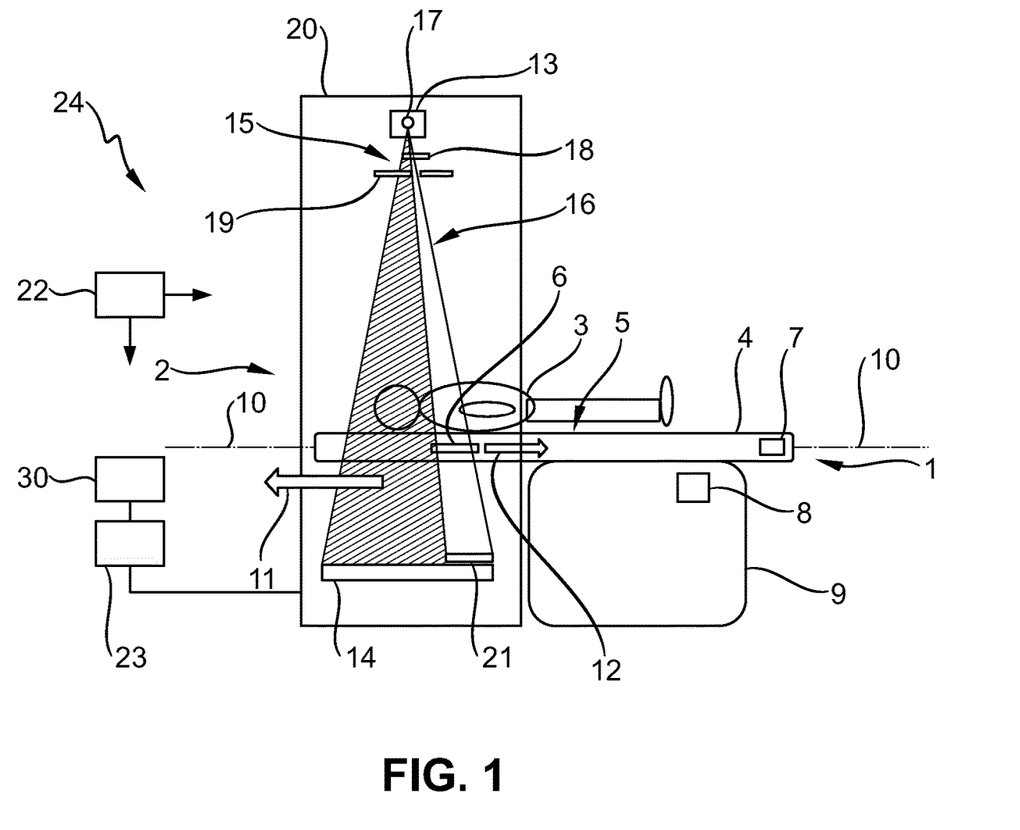
FIG. 1 shows schematically and exemplarily an embodiment of a computed tomography imaging system for generating a computed tomography image of a subject.

FIG. 1 shows schematically and exemplarily an embodiment of a computed tomography imaging system for generating a computed tomography image of a subject. The computed tomography imaging system 24 comprises a projection data acquisition apparatus 2 for acquiring projection data of the subject 3 and a reconstruction unit 23 for reconstructing the computed tomography image based on the acquired projection data. The projection data acquisition apparatus 2 comprises a subject support device 1 for supporting the subject 3 while acquiring the projection data and an x-ray tube 13 with a focal spot 17 for providing x-rays 15 for traversing the subject 3 and for traversing a diffraction grating 6 of the subject support device 1. The projection data acquisition apparatus 2 further comprises an x-ray detector 14 for detecting the x-rays 15 after having traversed the subject 3 and the diffraction grating 6 and for generating the projection data based on the detected x-rays. In this embodiment the diffraction grating 6 is a phase grating, which could also be named phase-shifting grating. However, in another embodiment the diffraction grating could also be an absorption grating.

The projection data acquisition apparatus 2 further comprises an absorption grating 21 which is arranged such that the x-rays traverse the absorption grating 21, after the subject 3 and the diffraction grating 6 have been traversed by the x-rays, wherein the x-ray detector 14 detects the x-rays after having traversed the subject 3, the diffraction grating 6 and the absorption grating 21 for generating the projection data. The projection data acquisition apparatus 2 further comprises a collimator 19 for collimating the x-rays 15 generated by the x-ray tube 13 such that the dimensions of the collimated x-rays 16 correspond to the dimensions of the diffraction grating 6 and the absorption grating 21. This allows for a reduction of the radiation dose applied to the subject 3, if phase-contrast and/or dark-field projection data are to be generated by the projection data acquisition apparatus 2.

The projection data acquisition apparatus 2 also includes a third grating 18 mounted close to the x-ray tube 13 for dividing the x-rays into an array of sources with a spatial coherence which allows for the generation of the phase-contrast and/or dark-field projection data. The third grating 18 can be arranged between the x-ray tube 13 and the collimator 19 or between the collimator 19 and the subject 3. The third grating is preferentially also an absorption grating.

The x-ray tube 13, the x-ray detector 14, the absorption grating 21, the third grating 18 and the collimator 19 are arranged on a rotatable gantry 20 which is adapted to rotate around the subject 3. For generating the phase-contrast or dark-field projection data the gantry 20 can be rotated to a rotational position as schematically and exemplarily illustrated in FIG. 1, wherein the subject 3 can be arranged outside of an interferometer formed by the diffraction grating 6 and the absorption grating 21. However, for generating the phase-contrast and/or dark-field projection data the gantry 20 can also be rotated to another rotational position. For instance, the gantry 20 can be rotated such that the x-ray tube 13 is below the subject 3 and the x-ray detector with the absorption grating 21 is above the subject 3. In this case the subject 3 is located within the interferometer formed by the diffraction grating 6 and the absorption grating 21.

The subject support device 1 comprises a support component 4 providing a support surface 5 for supporting the subject 3 while acquiring the projection data. The subject support device 1 further comprises the diffraction grating 6 for diffracting the x-rays, which is integrated in the support component 4, and a moving unit for moving the support component 4 and the diffraction grating 6 relative to each other. In this embodiment a first motor 7 is used for moving the diffraction grating 6 in a first longitudinal direction 12 relative to the subject component 4 and a second motor 8 is used for moving the support component 4 in a second longitudinal direction 11 being opposite to the first longitudinal direction 12. The first and second longitudinal directions 11, 12 are parallel to the longitudinal axis 10 of the support component 4 which corresponds to the rotational axis or z axis of the computed tomography imaging system 24.

The first and second motors 7, 8 are components of the moving unit, wherein the second motor 8 is adapted to move the support component 4 relative to a support foot 9 in the second longitudinal direction 11 and wherein at the same time the first motor 7 moves the diffraction grating 6 in the first longitudinal direction 12 relative to the support component 4 such that the diffraction grating 6 remains stationary relative to the support foot 9. This coordinated movement of the support component 4 and the diffraction grating 6 allows the collimated x-rays 16 to traverse a) different parts of the subject 3 and the x-ray detector 14 to generate phase-contrast and/or dark-field projection data of the different parts of the subject 3 and b) the stationary diffraction grating 6. The generated projection data can then be combined by the reconstruction unit 23 for generating a projection image showing the different parts of the subject 3. The reconstruction unit 23 can therefore also be regarded as being an image generation unit for generating such a projection image. Moreover, since the image generation unit 23 is adapted to generate a projection image showing the different parts of the subject 3, it can also be regarded as being a part of the projection data acquisition apparatus 2.

The reconstruction of the computed tomography image and the generation of the projection image showing the different parts of the subject 3 can also be performed by two separate units, wherein a first unit may be adapted to reconstruct a computed tomography image and a second unit may be adapted to generate a projection image showing the different parts of the subject. The projection image showing the different parts of the subject can be regarded as being a phase-contrast or dark-field scout image or a phase-contrast or dark-field radiography image.

The moving unit can further be adapted to move the diffraction grating 6 in a direction being transverse to the longitudinal axis 10 such that x-rays generated by the x-ray tube 13 can be detected by the x-ray detector 14, after they have traversed the subject 3, but not the diffraction grating 6. It is also possible that not the moving unit is used to move the diffraction grating 6 in a direction being transverse to the longitudinal axis 10, but that it is manually movable in this direction. Also the absorption grating 21 can be, for instance, manually movable such that the x-rays generated by the x-ray tube 13 can be detected by the x-ray detector 14, wherein the detected x-rays have not traversed the absorption grating 21. Thus, the gratings 6, 21 are movable out of the beam produced by the x-rays generated by the x-ray tube 13. Also the third grating 18 is preferentially movable out of this beam.

The projection data acquisition apparatus 2 is adapted to generate attenuation projection data in different acquisition directions, if the gratings 6, 18, 21 have been moved out of the x-ray beam, wherein in this case the reconstruction unit 23 reconstructs absorption computed tomography images of the subject 3 based on the acquired attenuation projection data. For this reconstruction known reconstruction algorithms can be used like a filtered back projection algorithm, a Radon inversion algorithm, et cetera.

For generating the attenuation projection data the collimator 19 is preferentially adjusted such that the entire x-ray detector 14 is illuminated by the x-rays 15 generated by the x-ray tube 13. However, also when generating the attenuation projection data the x-rays 15 generated by the x-ray tube 13 can be collimated such that only a part of the x-ray detector 14 is illuminated by the x-rays.

Since the gratings are movable into and out of the x-ray beam generated by the x-rays of the x-ray tube 13, the computed tomography imaging system 24 with the projection data acquisition apparatus 2 can be adapted to generate a) attenuation projection data and absorption computed tomography images and b) also phase-contrast and/or dark-field projection data, wherein the phase-contrast and/or dark-field projection data can be used for generating a projection image showing different parts of the subject 3, i.e. for generating a phase-contrast or dark-field scout image or phase-contrast or dark-field radiography image showing the entire subject 3 or a portion of the subject 3 being larger than a part of the subject 3 which can be traversed at a same time by the x-rays.

Phase-contrast and/or dark-field projection data are obtained from the raw data in a known way by means of so-called phase retrieval. Basically, the intensity measured by each detector can be modeled by using following equation:

$$I=I_0 T(1+V_0 D \cos(\alpha_0+\varphi)),$$

wherein I is the intensity detected by the x-ray detector 14, $I_0$ is the blank scan intensity, i.e. the intensity, which is detected, if the subject is not traversed, T is the attenuation, $V_0$ is the fringe visibility, D is the dark field signal, $\alpha_0$ is the fringe phase and $\varphi$ is the phase shift caused by the subject. Based on this model and by measuring the intensity I several times for different phases $\alpha_0$, the attenuation T, the dark field signal D, i.e. the dark field projection data, and the phase shift $\varphi$, i.e. the phase contrast projection data, can be determined. For more details regarding the known technique for determining the dark field projection data and the phase contrast projection data reference is made to, for instance, the article "Grating interferometer based scanning setup for hard x-ray phase contrast imaging" by C. Kottler et al., Review of Scientific Instruments, volume 78(4) (2007), which is herewith incorporated by reference, wherein the third grating 18 corresponds to the grating $G_0$ mentioned in the article, the diffraction grating 6 corresponds to the phase grating $G_1$ mentioned in the article and the absorption grating 21 corresponds to the absorption grating $G_2$ mentioned in the article. This technique neglects the cone angle such that for small cone angles very accurate projection data can be obtained. If the cone angle should not be neglected, other known techniques can be used for determining the dark field and phase contrast projection data. For instance, a tomosynthesis type acquisition technique can be used for determining the projection data, wherein these projection data can be three-dimensionally reconstructed as disclosed in the articles "X-ray phase-contrast tomosynthesis for improved breast tissue discrimination" by S. Schleede S et al., European Journal of Radiology, volume 83, pages 531 to 536 (2014) or "Correction of data truncation artifacts in differential phase contrast (DPC) tomosynthesis imaging" by J. Garrett et al., Physics in Medicine and Biology, volume 60, pages 7713 to 7728 (2015), which are herewith incorporated by reference.

The x-ray detector preferentially comprises detection hardware for detecting the x-rays and for generating the raw data being indicative of the intensity of the detected x-rays. For processing these raw data for generating the phase contrast projection data and/or the dark field projection data a correspondingly configured processor can be used, wherein this processor is preferentially regarded as being a part of the x-ray detector, even if it is spatially separated from the detection hardware. This processor can be integrated with the detection hardware, or, as indicated above, it can be separate from the detection hardware. For instance, it can be a unit, which is spatially separated from the detection hardware, wherein the raw data are transmitted to the processor via a wired and/or wireless data connection, in order to allow the processor to generate the phase contrast projection data and/or the dark field projection data based on the raw data. The processor can also be integrated in another unit like the image generation unit.

Figure 2:
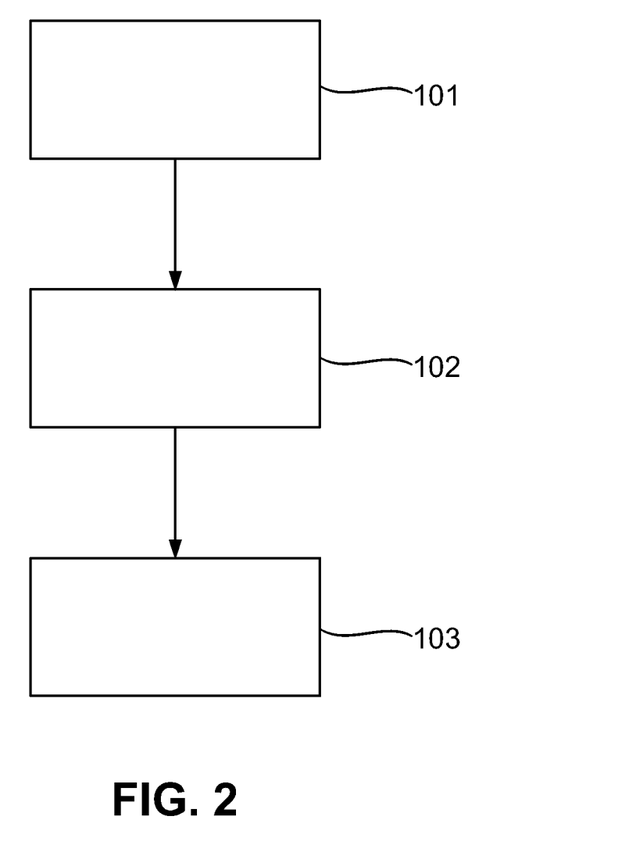
FIG. 2 shows a flowchart exemplarily illustrating an embodiment of a projection data acquisition method for acquiring projection data of a subject.

In the following an embodiment of a projection data acquisition method for acquiring projection data of a subject will exemplarily be described with reference to a flowchart shown in FIG. 2.

In step 101 the subject 3 is supported by using the subject support device 1 and the support component 4 of the subject support device 1 is moved in the second longitudinal direction 11, while the diffraction grating 6 is moved relative to the support component 4 in the opposite first direction 12 such that the subject 3 is moved in the second longitudinal direction 11 relative to the support foot 9 and the diffraction grating 6 remains stationary relative to the support foot 9. Moreover, the x-ray tube 13 generates x-rays traversing the further grating 18, the collimator 19, the subject 3, the diffraction grating 6 and the absorption grating 21 before being detected by the x-ray detector 14, in order to allow the x-ray detector 14 to generate phase-contrast and/or dark-field projection data for different parts of the subject 3. In step 102 the image generation unit 23 generates a phase-contrast projection image and/or a dark-field projection image showing the different parts of the subject 3 based on the phase-contrast and/or dark-field projection data, respectively, generated in step 101. In step 103 the generated phase-contrast projection image and/or the generated dark-field projection image, respectively, is shown on a display 30.

The computed tomography imaging system 24 further comprises a controller 22 for controlling the different parts of the computed tomography imaging system 24 and hence of the projection data acquisition apparatus 2 and of the subject support device 1. The controller 22 can comprise several sub controllers for providing different control functionalities. In particular, a first sub controller can be provided for controlling the components of the subject support device 1 and a second sub controller can be provided for controlling the components of the projection data acquisition apparatus 2 not being components of the subject support device 1.

The computed tomography imaging system is preferentially adapted to generate a phase-contrast projection image and/or a dark-field projection image of the lung of the subject. Large field of view phase-contrast and dark-field imaging of the lungs is generally problematic, because of, for instance, an implementation of a scanning geometry which is atypical for radiography systems, or difficulties in providing a large area gapless tiling of gratings to cover the relatively large field of view of, for example, 43 cm×43 cm. However, the scanning implementation can be quite naturally integrated into the hardware functionality already provided by known absorption computed tomography imaging systems by equipping these known absorption computed tomography imaging systems with the gratings 6, 18, 21 which are movable into and out of the x-rays generated by the x-ray unit 13. In particular, these gratings can be retractably integrated in existing absorption computed tomography imaging systems for providing a two-dimensional scout functionality for phase-contrast and dark-field imaging without compromising the conventional, non-phase-contrast and non-dark-field computed tomography performance.

The phase grating 6, i.e. the diffraction grating, is integrated in the support component 4, which is preferentially a patient table, wherein during the actuation of the support component 4 to perform the scout scan, the phase grating 6 is actuated inside the support component 4 in an opposite direction in order to maintain a constant position in the longitudinal direction which might also be regarded as being a z direction. The x-ray tube 13 is preferentially located directly above or below the subject 3 and vice versa for the x-ray detector 14. In the former case the preferred geometry is the normal geometry with the subject 3 outside of the interferometer formed by the diffraction grating 6 and the absorption grating 21, while in the latter case the inverse geometry is preferred. By using the embodiments described above with reference to FIG. 1 several advantages can be achieved in comparison to, for instance, known two-dimensional radiography dark-field x-ray (DAX) systems. For instance, the scanning hardware is available already in existing absorption computed tomography imaging systems. Moreover, the gratings can be designed essentially one-dimensionally with a very limited coverage in the longitudinal direction or z direction, because the grating coverage in the longitudinal direction or z direction must only provide for the option to use adjacent readings in this direction for the purpose of phase retrieval as disclosed in the above mentioned article by C. Kottler et al. In particular, keeping in mind the above basic model for signal generation, $I=I_0T(1+V_0D \cos(\alpha_0+\varphi))$, it is clear that in this example at least three measurements are required in order to obtain sufficient information to retrieve the three unknowns, i.e. the attenuation T, the dark field signal D and the phase shift $\varphi$. However, preferentially, more than three, for instance eight or twelve measurements are obtained. For a fixed fringe pattern, this implies that the beam collimation is preferentially wide enough to illuminate at least three rows of detection elements of the x-ray detector, but preferentially more, for instance eight or twelve rows. Thus, the coverage in the z direction, i.e. in the longitudinal direction, can be relatively small.

Moreover, detector frame times for computed tomography are much shorter than in radiography where single-shot imaging is still very common and high frame times for phase retrieval are more difficult to realize. In particular, several intensity measurements are preferentially taken for a particular ray, wherein the cone angle is preferentially ignored, while the subject is moved through the x-ray beam. The high frame rate of the detector, which is generally present in computed tomography systems, facilitates a quick motion of the subject even for a small cone angle. A further advantage of the high frame rate is that the system becomes less susceptible to vibrations, which could generally lead to an undesired blurring of the fringe pattern generated by the gratings.

In order to not compromise conventional computed tomography performance, the gratings hardware is preferentially designed to be inserted or retracted depending on the intended use as a, for instance, phase-contrast scout radiography or conventional computed tomography scan. In particular, the third grating 18 can be actuated into or out of the x-ray beam with rather small displacements in view of the closeness to the x-ray tube 13.

Although in above described embodiments it is mentioned that also the third grating 18 can be moved out of the x-ray beam, it is also possible that the third grating 18 remains within the x-ray beam during an absorption computed tomography procedure. In particular, the third grating 18 might not be movable out of the x-ray beam. In this case higher x-ray intensities, i.e. higher tube currents, can be employed, in order to compensate for the reduction in available x-ray flux due to the third grating 18 still located in front of the x-ray tube 13.

The third grating 18 is preferentially adapted such that it does not alter the spectral properties of the x-rays generated by the x-ray tube 13 or alters the spectral properties as desired. For instance, the third grating 18 can comprise carrier material with a titan sheet, wherein the carrier material can be chosen such that desired spectral properties are obtained. The carrier material can be, for example, graphite or silicon.

The third grating 18 is preferentially an absorption grating with grating bars having an attenuation in the order of 80 to 100 percent. Trenches between the grating bars are preferentially designed to transmit about 100 percent of the x-rays.

The computed tomography imaging system described above with reference to FIG. 1 can be obtained by equipping an existing absorption computed tomography imaging system with the gratings and the moving unit for moving the diffraction grating relative to the support component, i.e. in particular the patient table. Thus, computed tomography imaging systems already in the field can be retrofitted, in order to obtain a computed tomography imaging system which is also able to generate, for instance, phase-contrast and/or dark-field radiography or scout images.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the generation of the projection data, the generation of a projection image, the reconstruction of a computed tomography image, et cetera performed by one or several units or devices can also be performed by any other number of units or devices. These operations and/or the control of the projection data acquisition apparatus in accordance with the projection data acquisition method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a subject support device to be used in a projection data acquisition apparatus for acquiring projection data of a subject. The subject support device comprises a support component providing a support surface for supporting the subject while acquiring the projection data, a diffraction grating for diffracting x-rays, and a moving unit for moving the support component and the diffraction grating relative to each other. This relative movement can allow for a movement of the support component such that the subject is moved through x-rays for determining projection data of different parts of the subject, while the diffraction grating can still be traversed by the x-rays. These projection data can be used for generating a relatively large phase-contrast and/or dark-field projection image.

The invention claimed is:

1. A subject support device for use in a projection data acquisition apparatus for acquiring projection data of a subject, the subject support device comprising:
a support component providing a support surface configured to support the subject while acquiring the projection data;
a diffraction grating configured to diffract x-rays; and
a mover configured to move, at the same time, the support component and the diffraction grating relative to each other on the same plane.

2. The subject support as defined in claim 1, wherein the mover is configured to move the support component and the diffraction grating in opposite directions.

3. The subject support as defined in claim 1, wherein the diffraction grating is integrated in the support component.

4. The subject support device as defined in claim 1, wherein the subject support device comprises a support foot to be positioned on a floor, wherein the mover is configured to move at least one of the support component and the diffraction grating relative to the support foot.

5. The subject support device as defined in claim 1, wherein the support component comprises a longitudinal axis, and wherein the mover is configured to move at least one of the diffraction grating and the support component parallel to the longitudinal axis.

6. The subject support device as defined in claim 1, wherein the support component comprises a longitudinal axis, and wherein the mover is configured to move the diffraction grating in a direction that is transverse to the longitudinal axis.

7. The subject support as defined in claim 1, the mover comprising a first mover and a second mover, and wherein the second mover is configured to move the support component and at the same time the first mover moves the diffraction grating.

8. The subject support device as defined in claim 4, wherein the mover is configured to move at least one of the support component and the diffraction grating such that the diffraction grating remains stationary relative to the support foot.

9. A projection data acquisition apparatus for acquiring projection data of a subject, the projection data acquisition apparatus comprising:
a subject support device comprising:
a support component providing a support surface configured to support the subject while acquiring the projection data;
a diffraction grating configured to diffract x-rays; and
a mover configured to move, at the same time, the support component and the diffraction grating relative to each other on the same plane;
an x-ray tube configured to provide x-rays for traversing the subject and the diffraction grating of the subject support device; and
an x-ray detector configured to detect the x-rays after having traversed the subject and the diffraction grating and configured to generate the projection data based on the detected x-rays.

10. The projection data acquisition apparatus as defined in claim 9, further comprising a further grating configured such that the x-rays traverse the further grating after the subject and the diffraction grating have been traversed by the x-rays, and wherein the x-ray detector is configured to detect the x-rays after having traversed the subject, the diffraction grating, and the further grating.

11. The projection data acquisition apparatus as defined in claim 9, wherein the subject support device comprises a support foot to be positioned on a floor, wherein the projection data acquisition apparatus comprises a controller configured to control the subject support device such that the mover of the subject support device moves the support component relative to the support foot and relative to the x-ray tube in order to allow the x-rays to traverse different parts of the subject and the x-ray detector to generate projection data of the different parts of the subject, while the diffraction grating remains stationary relative to the support foot and relative to the x-ray tube in order to allow the x-rays to traverse the diffraction grating while traversing the different parts of the subject.

12. The projection data acquisition apparatus as defined in claim 11, further comprising an image generator configured to generate a projection image showing the different parts of the subject based on the generated projection data.

13. A computed tomography imaging system for generating a computed tomography image of a subject, the computed tomography imaging system comprising:
a projection data acquisition apparatus comprising:
a subject support device comprising:
a support component providing a support surface configured to support the subject while acquiring the projection data;
a diffraction grating configured to diffract x-rays; and
a mover configured to move, at the same time, the support component and the diffraction grating relative to each other on the same plane;
an x-ray tube configured to provide x-rays for traversing the subject and the diffraction grating of the subject support device; and an x-ray detector configured to detect the x-rays after having traversed the subject and the diffraction grating and configured to generate the projection data based on the detected x-rays, wherein the diffraction grating is movable such that the x-rays provided by the x-ray tube do not traverse the diffraction grating, wherein the projection data acquisition apparatus is configured to rotate the x-ray tube around the support component in order to allow the x-rays generated by the x-ray tube to traverse the subject in different acquisition directions and the x-ray detector to generate projection data corresponding to the different acquisition directions; and a reconstructor configured to reconstruct the computed tomography image based on the acquired projection data.

14. A projection data acquisition method for acquiring projection data of a subject by using a projection data acquisition apparatus, the projection data acquisition method comprising:

supporting the subject by using a subject support device of the projection data acquisition apparatus;

moving, at the same time, a support component of the subject support device and a diffraction grating of the subject support device relative to each other on the same plane while acquiring the projection data;

providing x-rays for traversing the subject and the diffraction grating by an x-ray tube of the projection data acquisition apparatus;

detecting the x-rays after having traversed the subject and the diffraction grating; and generating the projection data based on the detected x-rays by an x-ray detector of the projection data acquisition apparatus.

15. A non-transitory computer-readable medium having one or more executable instructions stored thereon, which, when executed by processor circuitry, cause the processor circuitry to perform a projection data acquisition method for acquiring projection data of a subject by using a projection data acquisition apparatus, the projection data acquisition method comprising:

supporting the subject by using a subject support device of the projection data acquisition apparatus;

moving, at the same time, a support component of the subject support device and a diffraction grating of the subject support device relative to each other on the same plane while acquiring the projection data;

providing x-rays for traversing the subject and the diffraction grating by an x-ray tube of the projection data acquisition apparatus;

detecting the x-rays after having traversed the subject and the diffraction grating; and generating the projection data based on the detected x-rays by an x-ray detector of the projection data acquisition apparatus.

* * * * *